United States Patent
Silverman et al.

(10) Patent No.: US 10,314,307 B2
(45) Date of Patent: *Jun. 11, 2019

(54) (S)-ABSCISIC ACID DERIVATIVES FOR IMPROVING PLANT STRESS TOLERANCE

(71) Applicant: Valent BioSciences Corporation, Libertyville, IL (US)

(72) Inventors: Franklin Paul Silverman, Highland Park, IL (US); Gary T. Wang, Libertyville, IL (US); Kimberly Ann Falco, Crystal Lake, IL (US); Derek D. Woolard, Zion, IL (US); Dale O. Wilson, Jr., Round Laked Beach, IL (US); Daniel C. Leep, Lindenhurst, IL (US); Gregory D. Venburg, Deerfield, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,813

(22) Filed: May 19, 2016

(65) Prior Publication Data
US 2016/0338353 A1 Nov. 24, 2016

Related U.S. Application Data

(60) Provisional application No. 62/163,620, filed on May 19, 2015.

(51) Int. Cl.
*A01N 37/42* (2006.01)
*A01N 37/06* (2006.01)
*C07C 403/20* (2006.01)

(52) U.S. Cl.
CPC ............ *A01N 37/42* (2013.01); *A01N 37/06* (2013.01); *C07C 403/20* (2013.01); *C07C 2601/16* (2017.05)

(58) Field of Classification Search
None
See application file for complete search history.

(56) References Cited

U.S. PATENT DOCUMENTS

| | | | |
|---|---|---|---|
| 9,326,508 B2 | 5/2016 | Wang et al. | |
| 2008/0184395 A1* | 7/2008 | Zhu | C12N 9/13 800/289 |
| 2012/0088667 A1* | 4/2012 | Williams | A01N 25/32 504/105 |
| 2014/0087949 A1 | 3/2014 | Frackenpohl et al. | |

FOREIGN PATENT DOCUMENTS

| | | | | |
|---|---|---|---|---|
| EP | 0371882 A2 * | 6/1990 | | A01N 37/36 |
| WO | WO1994/015467 | 7/1994 | | |
| WO | WO-2007008580 A1 * | 1/2007 | | A01N 37/42 |

OTHER PUBLICATIONS

K. Ueno et al., "Differences between the structural requirements for ABA 8'-hydroxylase inhibition and for ABA activity," Bioorganic & Medicinal Chemistry 13 (2005) 3359-3370.*
Y. Todoroki et al., "3'-Azidoabscisic Acid as a Photoaffinity Reagent for Abscisic Acid Binding Proteins," Bioorganic & Medicinal Chemistry Letters 11 (2001) 2381-2384.*
The Free Dictionary, "Crop," http://www.thefreedictionary.com/crop, Copyright 2016, p. 1-7.*
International Search Report and Written Opinion dated Aug. 25, 2016 in corresponding PCT Application No. PCT/US2016/033172.
Huang et al., The relationship of drought-related gene expression in *Arabidopsis thaliana* to hormonal and environmental factors, J Exp Bot. 2008;59(11):2991-3007.

* cited by examiner

*Primary Examiner* — Monica A Shin
(74) *Attorney, Agent, or Firm* — Wood, Phillips, Katz, Clark & Mortimer

(57) ABSTRACT

The present invention is directed to the treatment of crop plants with 3'-methyl-(S)-abscisic acid, 3'-propargyl-(S)-abscisic acid, and/or salts thereof in order to improve the plants' environmental stress tolerance.

4 Claims, No Drawings

(S)-ABSCISIC ACID DERIVATIVES FOR IMPROVING PLANT STRESS TOLERANCE

FIELD OF THE INVENTION

The present invention is directed to methods for protecting plants from environmentally stressful conditions comprising applying (S)-abscisic acid ("S-ABA") derivatives to the plants.

BACKGROUND OF THE INVENTION

During their life cycle, plants may be at risk for exposure to environmentally stressful conditions. These conditions can include exposure to low temperatures and limited access to water (such as drought). If the duration or severity of these stressful conditions is too great, the exposed plants may have reduced growth and yield. While plants have mechanisms to mitigate the effects of environmentally stressful conditions, continuous exposure may cause damage to the plants and can result in death of the plant. Reduced crop yield or death of crop plants due to environmentally stressful conditions is a major concern of plant growers.

Crop growers desire to plant their crops as early as possible so that they can obtain the highest available yield during the growing season. Crop growers with a large acreage to plant also want to begin planting as soon as possible. Early planting, however, is not without risks. One risk is that the crops will be exposed to cold temperatures that may cause the seedlings or plants to suffer damage or death. Cold temperatures cause millions of dollars of damage to crops each year. In some parts of the United States, cold temperatures can occur at any time during the growing season. Cold temperature damage is most common, however, in the spring when the plants are vulnerable.

Unfortunately, if cold temperature damage occurs to a grower's crops, the grower is then faced with a dilemma. Currently growers must either replant their fields immediately, or wait for several days to see if their plants recover and then decide if they should replant their fields. If the growers wait for several days to see if their plants recover and the damaged plants do not, then they have wasted valuable time before replanting and further reduced their potential yields. If the plants appear to recover and the growers do not replant, then the growers will be concerned about the negative impacts on yield for the rest of the growing season. If the growers replant their crops, then they are spending valuable resources on damage mitigation that could have been spent elsewhere.

Drought is a common abiotic stress that limits the productivity of all major crops. About 80% of the agricultural land in the United States experienced drought in 2012, impacting 70 to 75% of corn and soybean acreage (United States Department of Agriculture, Economic Research Service, 2012). According to the United Nations, drought intensity is increasing worldwide (United Nations News Center, 2012). Even seasonal mild or moderate drought in critical growth stages can reduce yields by 20 to 50% on rain-fed farms or those with limited irrigation. According to the National Climatic Data Center, both moderate and severe to extreme drought is becoming more common. Coupled with the increasing depletion of water resources, there is a need for new products and solutions to meet drought stress. Several approaches are being used with varying levels of success to address this problem including agronomics, traditional plant breeding, genetic engineering and chemical treatments. Each of these strategies has potential benefits, but also significant shortcomings.

Chemicals that have been promoted and used commercially to alleviate the effects of drought in crop plants include abscisic acid, anti-transpirants, and triazole fungicides and growth inhibitors (e.g. tebuconazole). For example, anti-transpirants reduce gas exchange and thus inhibit water loss. However, reduction of gas exchange inhibits photosynthesis, and thus slows plant growth. Although these chemicals may be effective at combating drought, they may not be acceptable for use in field crops due to negative effects on yield, cost, adverse side effects, or short duration of effect.

Accordingly, there is a need for new methods for protecting crop plants from the stressors of low temperatures and drought. The new methods should be cost-effective for the growers and produce consistent and reliable protection.

SUMMARY OF THE INVENTION

The present invention is directed to methods for improving drought and cold temperature tolerance comprising applying 3'-methyl-(S)-abscisic acid, 3'-propargyl-(S)-abscisic acid, and salts thereof to crop plants.

DETAILED DESCRIPTION OF THE INVENTION

Recently, Applicant discovered new S-ABA derivatives (see U.S. patent application Ser. Nos. 62/022,037 and 14/593,597). Applicant determined that two derivatives were unexpectedly more potent than S-ABA. Specifically, these derivatives are (2Z,4E)-5-((S)-1-hydroxy-2,3,6,6-tetramethyl-4-oxocyclohex-2-en-1-yl)-3-methylpenta-2,4-dienoic acid ("3'-methyl-(S)-abscisic acid") and (2Z,4E)-5-((S)-1-hydroxy-2,6,6-trimethyl-4-oxo-3-(prop-2-yn-1-yl)cyclohex-2-en-1-yl)-3-methylpenta-2,4-dienoic acid ("3'-propargyl-(S)-abscisic acid"). The structures of these derivatives are below:

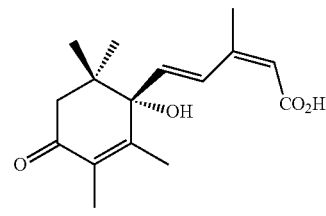

3'-methyl-(S)-abscisic acid

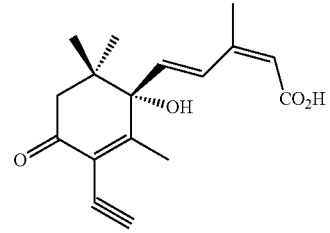

3'-propargyl-(S)-abscisic acid

Applicant unexpectedly found that the abscisic acid derivatives 3'-methyl-(S)-abscisic acid and 3'-propargyl-(S)-abscisic acid provided excellent improvement in tolerance of low temperatures and drought conditions. Specifically, Applicant found that 3'-methyl-(S)-abscisic acid was from about two to about ten times as effective as S-ABA when applied to crops plants to mitigate drought and chilling stress. 3'-Propargyl-(S)-abscisic acid has similar activity against drought and cold stress on crop plants.

In an embodiment, the present invention is directed to methods for improving low temperature tolerance comprising applying an abscisic acid derivative selected from the group consisting of 3'-methyl-(S)-abscisic acid, 3'-propargyl-(S)-abscisic acid, and a salt thereof to a crop plant.

In a preferred embodiment, the abscisic acid derivative applied to the crop plant to improve low temperature tolerance is 3'-methyl-(S)-abscisic acid.

In another embodiment, the 3'-methyl-(S)-abscisic acid is applied to improve low temperature tolerance at a rate of from about 2 to about 500 grams per hectare. In a preferred embodiment, the 3'-methyl-(S)-abscisic acid is applied at a rate of from about 5 to about 235 grams per hectare. In a more preferred embodiment, the 3'-methyl-(S)-abscisic acid is applied at a rate of from about 25 to about 85 grams per hectare.

In a further embodiment, the 3'-methyl-(S)-abscisic acid is applied to improve low temperature tolerance to a crop plant selected from the group consisting of corn, soybeans, cucumbers, tomato, tobacco, cotton, sorghum, peanut and rice. In a preferred embodiment, the crop plant is selected from the group consisting of corn, rice, sorghum and soybean. In a more preferred embodiment, the crop plant is corn or soybean.

In a preferred embodiment, the 3'-methyl-(S)-abscisic acid is applied to improve low temperature tolerance to the corn during the period beginning when the plants are at emergence and ending at reproductive stage. In a more preferred embodiment, the 3'-methyl-(S)-abscisic acid is applied to corn during the period beginning when the plants at emergence and ending at vegetative stage 10 (V10). In the most preferred embodiment, the 3'-methyl-(S)-abscisic acid is applied to corn during the period beginning when the plants are at vegetative stage 3 (V3) until vegetative stage 6 (V6).

In a further embodiment, the 3'-methyl-(S)-abscisic acid is applied to improve low temperature tolerance with another plant growth regulator to the plant. In a preferred embodiment, the plant growth regulator is selected from the group consisting of cytokinins, gibberellins, anti-gibberellin/triazole fungicide, auxins, organic acids, ethylene generators and ethylene biosynthesis inhibitors. In a more preferred embodiment, the plant growth regulator is selected from the group consisting of gibberellins, ethylene generators, and anti-gibberellin triazole fungicides.

In another embodiment, the amount of an anti-gibberellin/triazole fungicide that is applied is from about 100 to about 690 grams per hectare. In a preferred embodiment, the amount of the anti-gibberellin/triazole fungicide that is applied is from about 100 to about 180 grams per hectare.

In another preferred embodiment, the abscisic acid derivative applied to the crop plant to improve low temperature tolerance is 3'-propargyl-(S)-abscisic acid.

In another embodiment, the 3'-propargyl-(S)-abscisic acid is applied to improve low temperature tolerance at a rate of from about 2 to about 500 grams per hectare. In a preferred embodiment, the 3'-propargyl-(S)-abscisic acid is applied at a rate of from about 5 to about 235 grams per hectare. In a more preferred embodiment, the 3'-propargyl-(S)-abscisic acid is applied at a rate of from about 25 to about 85 grams per hectare. In a further embodiment, the 3'-propargyl-(S)-abscisic acid is applied to improve low temperature tolerance to a crop plant selected from the group consisting of corn, soybeans, cucumbers, tomato, tobacco, sorghum, rice and soybean. In a preferred embodiment, the crop plant is selected from the group consisting of corn, rice, sorghum and soybean. In a more preferred embodiment, the crop plant is corn.

In a preferred embodiment, the 3'-propargyl-(S)-abscisic acid is applied to improve low temperature tolerance to the corn during the period beginning when the plants at emergence and ending at V10. In the most preferred embodiment, the 3'-methyl-(S)-abscisic acid is applied to corn during the period beginning when the plants are at vegetative stage 3 (V3) until V6 stage.

In a further embodiment, the 3'-propargyl-(S)-abscisic acid is applied to improve low temperature tolerance with another plant growth regulator to the plant. In a preferred embodiment, the plant growth regulator is selected from the group consisting of cytokinins, gibberellins, anti-gibberellin/triazole herbicides, auxins, organic acids, ethylene generators and ethylene biosynthesis inhibitors. In a more preferred embodiment, the plant growth regulator is selected from the group consisting of gibberellins, ethylene generators, and anti-gibberellin triazole fungicides.

In another embodiment, the amount of an anti-gibberellin/triazole fungicide that is applied is from about 100 to about 690 grams per hectare. In a preferred embodiment, the amount of the anti-gibberellin/triazole fungicide that is applied is from about 100 to about 180 grams per hectare.

In an embodiment, the present invention is directed to methods for improving drought stress tolerance comprising applying an abscisic acid derivative selected from the group consisting of 3'-methyl-(S)-abscisic acid, 3'-propargyl-(S)-abscisic acid, and a salt thereof to a crop plant.

In a preferred embodiment, the abscisic acid derivative applied to the crop plant to improve drought stress tolerance is 3'-methyl-(S)-abscisic acid.

In another embodiment, the 3'-methyl-(S)-abscisic acid is applied to improve drought stress tolerance at a rate of from about 10 to about 2000 grams per hectare. In a preferred embodiment, the 3'-methyl-(S)-abscisic acid is applied at a rate of from about 90 to about 600 grams per hectare. In a more preferred embodiment, the 3'-methyl-(S)-abscisic acid is applied at a rate of from about 110 to about 380 grams per hectare.

In a further embodiment, the 3'-methyl-(S)-abscisic acid is applied to a crop plant selected from the group consisting of corn, soybeans, cucumbers, tomato, tobacco, sorghum, rice and soybean. In a preferred embodiment, the crop plant is selected from the group consisting of corn, rice, sorghum and soybean. In a more preferred embodiment, the crop plants are corn or soybean.

In a preferred embodiment, the 3'-methyl-(S)-abscisic acid is applied to the corn to improve drought stress tolerance during the period beginning when the plants are emerging and ending at late grain fill stage. In a more preferred embodiment, the 3'-methyl-(S)-abscisic acid is applied to the corn during the period beginning when the plants are from vegetative stage 3 (V3) and ending at reproductive stage 5 (R5), and most preferably beginning at tassel emergence (VT) and ending at reproductive stage 3 (R3).

In a further embodiment, the 3'-methyl-(S)-abscisic acid is applied to improve drought stress tolerance with another plant growth regulator to the plant.

In a preferred embodiment, the plant growth regulator is selected from the group consisting of cytokinins, gibberellins, anti-gibberellin/triazole herbicides, auxins, organic acids, ethylene generators and ethylene biosynthesis inhibitors. In a more preferred embodiment, the plant growth regulator is selected from the group consisting of gibberellins, ethylene generators and anti-gibberellin triazole fungicides.

In another embodiment, the amount of an anti-gibberellin/triazole fungicide that is applied is from about 100 to about 690 grams per hectare. In a preferred embodiment, the amount of the anti-gibberellin/triazole fungicide that is applied is from about 100 to about 180 grams per hectare.

In another preferred embodiment, the abscisic acid derivative applied to the crop plant to improve drought stress tolerance is 3'-propargyl-(S)-abscisic acid.

In another embodiment, the 3'-propargyl-(S)-abscisic acid is applied to improve drought stress tolerance at a rate of from about 10 to about 2000 grams per hectare. In a preferred embodiment, the 3'-methyl-(S)-abscisic acid is applied at a rate of from about 90 to about 600 grams per hectare. In a more preferred embodiment, the 3'-methyl-(S)-abscisic acid is applied at a rate of from about 110 to about 380 grams per hectare.

In a further embodiment, the 3'-propargyl-(S)-abscisic acid is applied to improve drought stress tolerance to a crop plant selected from the group consisting of corn, soybeans, cucumbers, tomato, tobacco, sorghum, rice and soybean. In a preferred embodiment, the crop plant is selected from the group consisting of corn, rice, sorghum and soybean. In a more preferred embodiment, the crop plants are corn and soybean.

In a preferred embodiment, the 3'-propargyl-(S)-abscisic acid is applied to improve drought stress tolerance to corn during the period beginning when the plants are emerging and ending at late grain fill stage. In a more preferred embodiment, the 3'-methyl-(S)-abscisic acid is applied to the corn during the period beginning when the plants are at vegetative stage 3 (V3) and ending at reproductive stage 5 (R5), and most preferably beginning at tassel emergence (VT) and ending at reproductive stage 3 (R3).

In a further embodiment, the 3'-propargyl-(S)-abscisic acid is applied to improve drought stress tolerance with another plant growth regulator to the plant. In a preferred embodiment, the plant growth regulator is selected from the group consisting of cytokinins, gibberellins, anti-gibberellin/triazole fungicides, auxins, organic acids, ethylene generators and ethylene biosynthesis inhibitors. In a more preferred embodiment, the plant growth regulator is gibberellins, ethylene generators and anti-gibberellin triazole fungicides, which reduce crop growth.

In another embodiment, the amount of an anti-gibberellin/triazole fungicide that is applied is from about 100 to about 690 grams per hectare. In a preferred embodiment, the amount of the anti-gibberellin/triazole fungicide that is applied is from about 100 to about 180 grams per hectare.

As used herein, "improving" means that the plant has more of the quality than the plant would have had it if it had not been treated by methods of the present invention.

As used herein, "low temperature tolerance" refers to mitigating the effects of low temperatures to the plant.

As used herein, "low temperature" refers to temperatures low enough to damage the plants including when the plant tissue freezes due to a frost or freezing air temperatures. Cold damage may occur below 12 degrees Celsius. A freeze occurs at temperatures below 0 degrees Celsius. A frost may occur when temperatures are above freezing, but microclimate conditions (such as soil depressions, lack of soil heat radiation, wind, etc.) contribute to make near freezing air temperatures freeze the plant tissue and cause damage.

As used herein, "drought stress tolerance" refers to mitigating the effects of water shortage to the plant.

Applicants have referred to corn developmental stages throughout the application as "V" stages. The "V" stages are designated numerically as V1, V2, V3, etc. In this identification system of V(n), (n) represents the number of leaves with visible collars. Each leaf stage is defined according to the uppermost leaf whose leaf collar is visible. "VT" refers to tassel emergence growth stage and is not an early vegetative stage of corn.

The abscisic acid derivatives claimed herein are enantiomerically pure "(5)" derivatives, meaning that "(2Z,4E)-5-((S)-1-hydroxy-2,3,6,6-tetramethyl-4-oxocyclohex-2-en-1-yl)-3-methylpenta-2,4-dienoic acid," "(2Z,4E)-5-((S)-1-hydroxy-2,6,6-trimethyl-4-oxo-3-(prop-2-yn-1-yl)cyclohex-2-en-1-yl)-3-methylpenta-2,4-dienoic acid," "3'-propargyl-(S)-abscisic acid," and "3'-methyl-(S)-abscisic acid" refer to derivatives comprising greater than 95% purity of the "(5)" enantiomer. This means that the compounds claimed herein are not "racemic" or "(±)." "Racemic" and "(±)" refer to derivatives with a relatively equal mixture of R/S enantiomers.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases. Suitable salts include inorganic salts such as the ammonium, lithium, sodium, potassium, magnesium and calcium salts and organic amine salts such as the triethanolamine, dimethylethanolamine and ethanolamine salts.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise.

The following examples are intended to illustrate the present invention and to teach one of ordinary skill in the art how to use the formulations of the invention. They are not intended to be limiting in any way.

EXAMPLES

In these studies, 3'-methyl-(S)-abscisic acid and 3'-propargyl-(S)-abscisic acid and S-ABA were tested for inducing resistance to crop stress. 3'-Methyl-(S)-abscisic acid and 3'-propargyl-(S)-abscisic acid were formulated as 4% (wt/wt) aqueous solutions, each with a pH around 7.0. (S)-Abscisic acid was formulated as a 10% (wt/wt) aqueous formulation.

Example 1: Cucumber Seedling Chilling

In these studies, 3'-methyl-(S)-abscisic acid was compared with (S)-abscisic acid on cucumber seedlings for prevention of chilling damage. Cucumber plants cv. 'Straight Eight' were grown for two weeks at 25° C. and were size matched into groups of three plants. Each group was sprayed with water+0.05% non-ionic surfactant (control), 100 ppm 3'-methyl-(S)-abscisic acid and surfactant, or 100 ppm S-ABA and surfactant until wet, respectively. For the spray solutions, 3'-methyl-(S)-abscisic acid was dissolved in 0.5% by volume DMSO in water.

Following the foliar treatment, plants were held for 48 hours at room temperature, then subjected to 4° C. for 96 hours, and then returned to 25° C. After the plants had been allowed to recover from the chilling treatments for 48 hours, the plants were rated for percent leaf area affected and new growth. Applicant found the plants treated with 3'-methyl-(S)-abscisic acid showed less damage and were more vigorous compared to the control or (S)-abscisic acid treated plants, as is shown in Table 1.

TABLE 1

Effect of foliar application of S-ABA or 3'-methyl-S-ABA on cucumber following chilling at 4° C.

| Treatment | Percent Leaf Area Affected | New Growth Rating[1] |
|---|---|---|
| Control | 81.67 | 0 |
| S-ABA, 100 mg/liter; 300 ug/plant | 33.33 | 1 |
| 3'-methyl-(S)-ABA, 100 mg/liter, 300 ug/plant | 16.67 | 2 |

New growth rating:
0 = No new growth;
1 = some new growth;
2 = new leaves

As seen in Table 1, this chilling assay indicates that 3'-methyl-(S)-ABA is more effective than S-ABA at mitigating chilling damage.

Example 2: Tobacco Plants Drought Assay

Tobacco plants cv. Xanthi-nc were grown for six weeks at 25° C. and were size matched into groups of four. Each plant group was drench-treated with 10 mL of water containing 0.5% DMSO (control), 0.3 mg, 1.0 mg or 3.0 mg/plant 3'-methyl-(S)-abscisic acid, or 0.3 mg, 1.0 mg or 3.0 mg/plant S-ABA, respectively. The plants were kept in the greenhouse and not watered, simulating drought conditions. After 18 days of water withdrawal, the plants in all treatment groups wilted. At that point, all the plants were watered again. The number of plants that wilted during each day of water withdrawal and the number of plants that recovered following the re-watering were recorded.

TABLE 2

Effect of S-ABA or 3'-methyl-(S)-ABA on tobacco plants subjected to drought

| Treatment | Percent of non-wilted plans on days after drench treatment and drought initiation | | | | | | Percent of plants recovered 3 days after re-watering |
|---|---|---|---|---|---|---|---|
| | Day 8 | Day 10 | Day 12 | Day 14 | Day 16 | Day 18 | |
| Control | 100% | 83% | 0% | 0% | 0% | 0% | 0% |
| S-ABA 0.3 mg/plant | 100% | 100% | 17% | 0% | 0% | 0% | 0% |
| S-ABA 1 mg/plant | 100% | 100% | 50% | 0% | 0% | 0% | 0% |
| S-ABA 3 mg/plant | 100% | 100% | 67% | 0% | 0% | 0% | 0% |
| 3'-methyl-(S)-ABA 0.3 mg/plant | 100% | 100% | 83% | 33% | 0% | 0% | 0% |
| 3'-methyl-(S)-ABA 1 mg/plant | 100% | 100% | 100% | 83% | 67% | 0% | 33% |
| 3'-methyl-(S)-ABA 3 mg/plant | 100% | 100% | 100% | 100% | 83% | 0% | 83% |

As seen in Table 2, the 3'-methyl-(S)-abscisic acid treatments significantly increased the life expectancy of the plants under the drought condition. Applicant found that plants treated with even the lowest amount (0.3 mg) of 3'-methyl-(S)-abscisic acid exhibited superior drought tolerance compared to the untreated control or the highest amount (3.0 mg) of S-ABA. The 3'-methyl-(S)-abscisic acid treatment significantly increased the life expectancy of the plant. Further, none of the untreated or S-ABA treated plants recovered once they were watered. In contrast, 83% of the plants treated with 3 mg of 3'-methyl-(S)-abscisic acid fully recovered.

Example 3: Corn Plant Chilling

Corn seeds of a 111 day, central corn belt variety were planted in 2-quart pots filled with medium. After the corn grew for 10 days in the greenhouse at 24±3° C. (V2 to V3 growth stage), the plants received a foliar spray application of aqueous solutions of the test compounds containing 0.25% non-ionic surfactant with a volume equivalent to 30 gallons/acre. After spraying, plants were moved back to the greenhouse for 2 days, then moved to a growth chamber kept at 10° C. with a 16:8 light:dark cycle (cold treatment). After 5 days in the cold, plants were returned to the greenhouse for 2 days before being harvested destructively. Results of the studies comparing the growth rate of plants treated with S-ABA with 3'-methyl-(S)-ABA during the experiment are shown in Table 3.

TABLE 3

Effect of S-ABA or 3'-methyl-(S)-ABA on growth rate of corn before, during and after chilling at 10° C.

| TRT mg/liter | g/acre | Growth Rate (cm/day) | | |
|---|---|---|---|---|
| | | Greenhouse 0-2 d post spray | Growth Chamber 10° C. 2-7 d post spray | Greenhouse 7-9 d post spray |
| Control | 0 | 4.155 | 0.836 | 3.595 |
| S-ABA 1000 mg/l | 113.7 | 4.315 | 0.766 | 3.270 |
| 3'-Methyl-(S)-ABA 30 mg/l | 3.4 | 3.725 | 1.092 | 2.650 |
| 3'-Methyl-(S)-ABA 100 mg/l | 11.4 | 4.290 | 1.084 | 2.795 |
| 3'-Methyl-(S)-ABA 300 mg/l | 34.1 | 3.645 | 0.990 | 3.565 |
| 3'-Methyl-(S)-ABA 1000 mg/l | 113.7 | 3.615 | 1.160 | 2.945 |

In these studies, plant growth was initially suppressed following spraying with 3'-methyl-(S)-abscisic acid. Surprisingly, 3'-methyl-(S)-abscisic acid maintained growth under cold (10° C.) conditions, while S-ABA, even at 1000 mg/l (113.7 g/acre) did not maintain growth under the cold conditions. In one of two studies leaf area was increased by S-ABA, and 3'-methyl-(S)-abscisic acid at 30, 100 and 300 mg/liter, but this was not repeatable across studies.

In additional studies, the effect of S-ABA and 3'-propargyl-(S)-ABA on corn growth rate in chilling studies was compared. The results are in Table 4 below.

TABLE 4

Effect of S-ABA or 3'-propargyl-(S)-ABA on growth rate of corn before, during and after chilling at 10° C.

| Treatment mg/liter | g/acre | Greenhouse 0-2 d post spray | Growth Chamber 10° C. 2-7 d post spray | Greenhouse 7-9 d post spray |
|---|---|---|---|---|
| Control | 0 | 3.361 | 1.129 | 2.183 |
| S-ABA 1000 mg/l | 113.7 | 3.156 | 1.249 | 2.161 |
| 3'-propargyl-(S)-ABA 30 mg/l | 3.4 | 3.239 | 1.258 | 1.978 |
| 3'-propargyl-(S)-ABA 100 mg/l | 11.4 | 2.294 | 1.173 | 2.489 |
| 3'-propargyl-(S)-ABA 300 mg/l | 34.1 | 2.544 | 1.033 | 2.500 |
| 3'-propargyl-(S)-ABA 1000 mg/l | 113.7 | 2.172 | 0.787 | 2.300 |

Growth Rate (cm/day)

Unlike 3'-methyl-(S)-ABA, 3'-propargyl-(S)-ABA did not maintain growth under cold stress, but did aid growth during stress recovery, particularly at the rates between 11.4 and 113.7 g/acre (100 to 1000 mg/l). This was unexpected, as S-ABA, even at rates of up to 1000 mg/liter (113.7 g/acre), did not aid recovery growth following stress.

Example 4: Corn Drought

Several responses were measured in the corn drought assays. These include stomatal conductance, leaf rolling (a sign of water stress), as well as fresh weight at harvest.

Corn Stomatal Conductance

In this greenhouse experiment, foliar spray treatments containing 3'-methyl-(S)-abscisic acid, 3'-propargyl-(S)-abscisic acid or (S)-abscisic acid were applied to corn plants to evaluate their effect on gas exchange, as measured through stomatal conductance. Corn plants of a commercial, 111 day, central corn belt variety were grown in the greenhouse under optimal conditions for five weeks and were size-matched into ten groups of five plants. Using an aerosol sprayer, each group was sprayed to drip (25 milliliters per plant) with solutions containing a non-ionic surfactant (0.125%, v/v) and water (control), 2.5 mg, 7.5 mg or 25 mg/plant 3'-methyl-(S)-abscisic acid, or 2.5 mg, 7.5 mg or 25 mg/plant 3'-propargyl-(S)-abscisic acid, or 7.5 mg, 25 mg or 75 mg/plant (S)-ABA, respectively. After spraying, plants were returned to the greenhouse for the duration of the experiment. Stomatal conductance was measured using an AP4 porometer (Delta T Devices, Cambridge, UK) and the conductance for each plant was recorded at approximately the same time of day (~10 AM) prior to treatment application as well as 1, 2, 5, 6, 9 and 16 days post-spraying. The results of this study are shown below in Table 5.

TABLE 5

Cumulative stomatal conductance measurements at several days post spraying expressed as a percent of control.

| Treatment | Average Stomatal Conductance (% of Control) | |
|---|---|---|
| | 6 DAS* | 16 DAS* |
| Control | 100.0 | 100.0 |
| 3'-Methyl-(S)ABA (100 ppm or 2.5 mg/plant) | 93.3 | 98.3 |
| 3'-Methyl-(S)ABA (300 ppm or 7.5 mg/plant) | 70.6 | 79.4 |
| 3'-Methyl-(S)ABA (1000 ppm or 25 mg/plant) | 69.6 | 74.5 |
| 3'-Propargyl-(S)ABA (100 ppm or 2.5 mg/plant) | 80.6 | 87.7 |
| 3'-Propargyl-(S)ABA (300 ppm or 7.5 mg/plant) | 74.3 | 77.9 |
| 3'-Propargyl-(S)ABA (1000 ppm or 25 mg/plant) | 56.0 | 59.0 |
| S-ABA (300 ppm or 7.5 mg/plant) | 88.5 | 89.3 |
| S-ABA (1000 ppm or 25 mg/plant) | 83.7 | 88.0 |
| S-ABA (3000 ppm or 75 mg/plant) | 61.3 | 62.5 |

*DAS = Days after spraying

When the data in Table 5 were analyzed by regression, the relative potencies resulting in a 25% reduction in transpiration were 1.97 or 4.83 times that seen with S-ABA for 3'-methyl-(S)-abscisic acid, or 3'-propargyl-(S)-abscisic acid, respectively.

Corn Plant Leaf Rolling Assay

This study was conducted as described above with the following exceptions. After spraying, plants were put back in the greenhouse and water was withheld for twelve days, simulating drought stress. The plants were then watered to saturation for three consecutive days before the plant shoots were cut at the soil surface and subsequently weighed in grams (fresh weight). Leaf-rolling data and fresh weight data were recorded for each plant following treatment application at the times specified below in Table 6.

TABLE 6

Leaf-rolling and shoot fresh weights following spray application of S-ABA, 3'-methyl-(S)-ABA, or 3'-propargyl-(S)-ABA

| Treatment | Average # of Rolled Leaves/Plant | | | Shoot Fresh Weight |
|---|---|---|---|---|
| | 5 DAS* | 6 DAS* | 8 DAS* | 15 DAS |
| Control | 2.8 | 4.4 | 8.4 | 230.9 |
| S-ABA (300 ppm or 7.5 mg/plant) | 2.8 | 2.6 | 8.4 | 258.9 |
| S-ABA (1000 ppm or 25 mg/plant) | 1.2 | 3.0 | 8.8 | 282.5 |
| S-ABA (3000 ppm or 75 mg/plant) | 0.0 | 0.2 | 7.2 | 301.7 |
| 3'-Methyl-(S)-ABA (100 ppm or 2.5 mg/plant) | 1.6 | 4.6 | 9.0 | 256.0 |
| 3'-Methyl-(S)-ABA (300 ppm or 7.5 mg/plant) | 2.0 | 3.6 | 8.4 | 276.6 |
| 3'-Methyl-(S)-ABA (1000 ppm or 25 mg/plant) | 1.6 | 2.2 | 7.2 | 373.4 |
| 3'-Propargyl-(S)-ABA (100 ppm or 2.5 mg/plant) | 1.8 | 3.8 | 7.2 | 263.9 |
| 3'-Propargyl-(S)-ABA (300 ppm or 7.5 mg/plant) | 1.8 | 3.6 | 8.0 | 313.1 |
| 3'-Propargyl-(S)-ABA (1000 ppm or 25 mg/plant) | 0.0 | 0.0 | 7.0 | 334.4 |

*DAS = Days after spraying

The leaf rolling data shows that spray applications with both high rates of S-ABA (75 mg/plant) were as effective at reducing leaf rolling as 25 mg of 3'-methyl-(S)-abscisic acid, or 3'-propargyl-(S)-abscisic acid. In contrast, the fresh weight data showed that the 3'-substituted-(S)-abscisic acid derivatives were considerably more active at preserving growth under drought than S-ABA. A regression of the fresh weight data and the associated potencies of the analogs demonstrate that the analogs were from 9.0 to 9.8 times as active as S-ABA at maintaining growth under drought conditions.

Example 5: Corn Plant Emergence

Corn seed of a common inbred parental line were treated using standard seed treatment equipment with water (control), 40 µg, 80 µg or 160 µg/seed S-ABA, 10 µg, 20 µg, 40 µg or 80 µg/seed 3'-methyl-(S)-abscisic acid, or 10 µg, 20 µg, 40 µg or 80 µg/seed 3'-propargyl-(S)-abscisic acid. Post treatment, the seeds were planted in 12×3×2" plastic boxes containing one kilogram of sieved, pre-moistened field soil. Fifty seeds were planted in each box at three centimeter depth and two replicate boxes per treatment at 20.5° C. under constant illumination. Two replications of the experiment were incubated under constant light in a 20.5° C. growth chamber. Emergence counts were recorded almost daily until seedling emergence had ceased (42 days). Daily counts were converted to proportions of the final emergence to estimate the median emergence time for each box. Results of this emergence assay are shown below in Table 8.

TABLE 8

Emergence of corn seeds treated with S-ABA, 3'-methyl-(S)-ABA or 3'-propargyl-(S)-ABA

| Treatment | Median Time to Emergence (days) | Delay in Median Emergence Time Compared to Control (days) |
| --- | --- | --- |
| Control | 4.8 | n/a |
| S-ABA (40 µg/seed) | 10.5 | 5.6 |
| S-ABA (80 µg/seed) | 13.0 | 8.2 |
| S-ABA (160 µg/seed) | 14.6 | 9.7 |
| 3'-Methyl-(S)-ABA (10 µg/seed) | 9.7 | 4.9 |
| 3'-Methyl-(S)-ABA (20 µg/seed) | 12.7 | 7.9 |
| 3'-Methyl-(S)-ABA (40 µg/seed) | 16.0 | 11.1 |
| 3'-Methyl-(S)-ABA (80 µg/seed) | 18.6 | 13.8 |
| 3'-Propargyl-(S)-ABA (10 µg/seed) | 13.4 | 8.6 |
| 3'-Propargyl-(S)-ABA (20 µg/seed) | 16.2 | 11.3 |
| 3'-Propargyl-(S)-ABA (40 µg/seed) | 21.0 | 16.2 |
| 3'-Propargyl-(S)-ABA (80 µg/seed) | 27.3 | 22.4 |

As seen in Table 8, seed treatments containing 3'-methyl-(S)-abscisic acid, 3'-propargyl-(S)-abscisic acid or S-ABA greatly increased the median time of emergence as compared to the control, in a dose dependent manner. Furthermore, Applicant unexpectedly discovered that both 3'-methyl-(S)-abscisic acid and 3'-propargyl-(S)-abscisic acid prolonged the delay in emergence when compared to S-ABA applied at equivalent rates. For example, at 80 µg/seed rate, 3'-methyl-(S)-abscisic acid extended the delay in emergence by an average of 5.6 additional calendar days in comparison with S-ABA (13.8 versus 8.2 days), while 3'-propargyl-(S)-abscisic acid extended the delay an additional 14.3 calendar days (22.4 versus 8.2 days). A regression of dose required to delay the median emergence time by two days showed that the analogs were 2.2 and 2.6 times the relative potency of S-ABA for the 3'-methyl-(S)-abscisic acid and 3'-propargyl-(S)-abscisic acid, respectively.

Example 6: Soybean Drought Tolerance

In this study, soybean plants were grown for 10 days under ambient lab temperature conditions and illumination of 150 umol m$^2$ s$^{-1}$ and a 16:8 photoperiod. At spraying, the primary leaves were fully expanded and the first trifoliate leaves were partially expanded. The plants were sprayed to dampness with solutions of water, S-ABA, 3'-methyl-(S)-abscisic acid, or 3'-propargyl-(S)-abscisic acid containing 0.025% (v/v) non-ionic surfactant.

At times following spraying, the conductance of the primary leaves was measured using an AP4 porometer (Delta T Devices, Cambridge, UK) to evaluate the effect on stomatal conductance. A decrease in stomatal aperture, reflected in the conductance measures, is an immediate and direct effect of applied S-ABA. To simplify the data, the controls were always set to 100%. In Table 9, the effect of spray applications on the stomatal conductance was measured.

TABLE 9

The effect of foliar application of S-ABA, 3'-methyl-(S)-ABA, or 3'-propargyl-(S)-ABA on stomatal conductance of soybean

| | Day 1 | Day 2 | Day 5 | Day 6 | Day 7 |
| --- | --- | --- | --- | --- | --- |
| Control | 100% | 100% | 100% | 100% | 100% |
| S-ABA (300 mg/l) 0.3 mg/plant | 42% | 56% | 80% | 108% | 122% |
| S-ABA (1000 mg/l) 1.0 mg/plant | 27% | 32% | 58% | 80% | 118% |
| 3'-Methyl-(S)ABA (300 mg/l) 0.3 mg/plant | 11% | 18% | 36% | 68% | 79% |
| 3'-Propargyl-(S)-ABA (300 mg/l) 0.3 mg/plant | 8% | 14% | 33% | 52% | 57% |

*Percent Conductance: All data have been normalized so the control at each time point is equal to 100% conductance.

The two 3'-substituted-(S)-abscisic derivatives showed both a greater magnitude and a longer duration of activity than was observed with S-ABA. The low rate of S-ABA (300 mg/1) only showed a 58% reduction in stomatal conductance at 1 day post spraying, while 3'-methyl-(S)-abscisic acid and 3'-propargyl-(S)-abscisic acid showed an 89% and 92% reduction, respectively. By day 2, the 300 mg/l S-ABA treatment had recovered greater than half of the control conductance, while a 50% recovery was observed with the 3'-substituted-(S)-abscisic acid derivatives at 6 days post application. This time was longer than was observed with 1000 mg/l of S-ABA, which showed greater than 50% recovery at day 5.

The decrease in stomatal conductance observed in response to the foliar treatments is an indicator of water use by the plants. Because most plant water loss is through the stomates, the ability to close the stomates to a greater amount and for a longer time, as was observed for the 3'-methyl-(S)-ABA and 3'-propargyl-(S)-ABA, is a significant improvement over the use of S-ABA, and could be used to increase drought tolerance.

The invention claimed is:
1. A method of improving low temperature tolerance consisting of applying a composition consisting of (2Z,4E)-5-((S)-1-hydroxy-2,3,6,6-tetramethyl-4-oxocyclohex-2-en-1-yl)-3-methylpenta-2,4-dienoic acid (3'-methyl-(S)-abscisic acid) and or a salt thereof as the only active ingredient and at least one adjuvant to a crop plant selected from the group consisting of cucumber, tobacco, corn and soybean, wherein the 3'-methyl-(S)-abscisic acid is applied at a rate of from about 2 to about 235 grams per hectare.

2. The method of claim 1 wherein the 3'-methyl-(S)-abscisic acid is applied at a rate of from about 3.4 to about 11.4 grams per hectare.

3. A method of improving drought stress tolerance consisting of applying a composition consisting of (2Z,4E)-5-((S)-1-hydroxy-2,3,6,6-tetramethyl-4-oxocyclohex-2-en-1-yl)-3-methylpenta-2,4-dienoic acid (3'-methyl-(S)-abscisic acid) or a salt thereof as the only active ingredient and at least one adjuvant to a crop plant selected from the group consisting of cucumber, tobacco, corn and soybean,
wherein the 3'-methyl-(S)-abscisic acid is applied at a rate of from about 90 to about 600 grams per hectare.

4. The method of claim 3 wherein the methyl-(S)-abscisic acid is applied at a rate of from about 110 to about 380 grams per hectare.

* * * * *